United States Patent [19]

Wikman-Coffelt

[11] Patent Number: 5,075,210

[45] Date of Patent: * Dec. 24, 1991

[54] PRESERVATION OF THE HEART FOR TRANSPLANTATION

[75] Inventor: Joan Wikman-Coffelt, Davis, Calif.

[73] Assignee: The Regents of the University of California, Oakland, Calif.

[*] Notice: The portion of the term of this patent subsequent to Nov. 19, 2008 has been disclaimed.

[21] Appl. No.: 455,580

[22] Filed: Dec. 21, 1989

[51] Int. Cl.$^5$ .................................................. A01N 1/02
[52] U.S. Cl. ............................................ 435/1; 435/2
[58] Field of Search ................................................ 435/1

[56] References Cited

U.S. PATENT DOCUMENTS 4,663,289  5/1987  Veech ................................. 435/240
4,959,319  9/1990  Skelnik et al. ......................... 435/1

OTHER PUBLICATIONS

Kane—Chem. Abst., vol. 108 (1988), p. 34411y.
Edakuni–Chem. Abst., vol. 86 (1977), p. 53350w.
Cornell—Chem. Abst., vol. 100 (1984), p. 49243d.

Primary Examiner—Sam Rosen
Attorney, Agent, or Firm—Hana Dolezalova

[57] ABSTRACT

A novel method for long-term preservation of heart for transplantation. The heart is perfused first with a preservation solution containing essentially pyruvate, inorganic salts providing ions to retain the cell action potential and optionally a protein, with the second perfusion solution containing the first preservation solution.

19 Claims, 4 Drawing Sheets

PRESERVATION OF THE HEART FOR TRANSPLANTATION

BACKGROUND OF THE INVENTION

1. Field of Invention

This invention concerns a novel and improved process for long-term preservation of the heart for transplantation. The preservation process comprise of perfusing the heart at a warm temperature with a first novel physiological solution containing pyruvate, under normal physiological conditions to remove blood, increase flow, and load the cells with pyruvate. A second cardioplegic solution containing pyruvate and alcohol is used to effect the vasolidation, the heart arrest and decrease of metabolism rate to a basal metabolic stage. The heart having a cannulated aorta and left ventricular chamber allowing diffusion of gases and media, is submerged and stored in the first solution for periods longer than 24 hours.

2. Related Disclosures

Organ transplantation, in particular heart transplantation has become an important tool in saving lives in patients with irreversibly diseased or damaged organs. With increasing incidence of the circulatory diseases in the populations, the heart transplantation is used more and more to preserve a life of otherwise healthy individuals with badly injured heart following the heart attack, myocardial infarction or other heart conditions. Consequently, a demand for organs suitable for transplantation has risen substantially.

There are primary requirements for the organ to be suitable for transplantation. First, the organ must be healthy. Second, it must be transplanted or transplantable in certain time in which it is possible to preserve its normal physiological function. Third, it must be immunologically acceptable to the organ recipient.

The first requirement can be only be met by the physician removing the organ from the donor's body. The third requirement is increasingly being made possible by improved understanding of immune mechanism and method for preventing organ rejection by the recipient's immune system. The pharmaceutical industry is constantly developing and designing new immunosuppressant drugs which allow the easier immunological matching of the donor and the recipient and prevent, as much as possible, the organ rejection by recipient. Drugs such as azathioprine, monoclonal antibody muromonab-CD3, cyclophosphamide, cyclosporine and other recently discovered drugs such as for example drug known as FK-506 which supposedly cuts the rejection rate 90% now allow the suppression of immune reactions for up to 6 months at which time the body of the recipient is able to substantially rebuild proteins in the transplanted organ with their own proteins thus making it more immunologically acceptable. Moreover, when the graft tissue becomes accommodated within recipient's body, it can be maintained with relatively small and reasonably well tolerated doses of immunosuppressive drugs.

Consequently, the only remaining obstacle for the successful transplantation of organs is the preservation of their anatomical and functional integrity, in particular the preservation of their normal function for any length of time. With geographical spread of possible donors over the whole world, the length of time longer than 24 hours for preservation is extremely important. This is particularly true for organs having a continuous life preserving function and/or high metabolic rate with high energy and oxygen demands. The heart is one of the unique organs which has both.

The main causes leading to death of the myocardial cells are ischemia, edema, acidosis, calcium overload, and a loss of the electrical potential across the membrane. Consequently, these causes must be either eliminated or ameliorated to such degree that they do not cause the death of cells.

The primary function of the heart is its continuous pumping of blood through the blood circulation system. That function depends on uninterrupted myocardial contractility which, in turn, depends on uninterrupted supply of energy and oxygen. Myocardial contractility must be preserved even during the time when the heart is removed from the donor and transplanted into the recipient. Since the contracting heart needs the constant supply of energy and oxygen, if these are not available, myocardial ischemia, caused by inadequate circulation of blood to the myocardium develops, which in turn results the cell death and in the in irreversible destruction of the myocardial contractility.

Preservation of myocardial function from ischemic injury during cardiac arrest is currently commonly achieved by hypothermia and perfusion with certain cardioplegic solutions of which the most widely used cardioplegic agent is cold potassium chloride (15 to 35 mEg/1) solution. However, the potassium chloride is known to cause vasoconstriction and combined with hypothermia, such cardioplegic solution does not allow for full flow and washout of tissue. *Ann. Chir. Gynecol.,* 76:22 (1987); *Postgraduate Med. J.,* 59:11 (1983); *Canad. Anaesth. Soc. J.,* 27:381 (1980); *J. Suro. Res.,* 43:179 (1987).

Cardiac surgical procedures including a removal of the heart for transfusion and inserting the heart to the donor body often require a bloodless, relaxed and motionless field during operation. This is easily accomplished by ischemic arrest induced by cross clamping the aorta which accelerates ischemia and prevents exchange of gases. Any period of ischaemia accompanied therefore by oxygen deficiency causes metabolic and structural changes which determine the functional recovery of the heart in the postoperative period. The safe period of ischaemia for the human heart is not clearly defined but 20–30 minutes is generally considered to be the upper limit. When aortic cross clamping time exceeds this period, substantial subendocardial necrosis may occur, with low output syndrome in the postoperative period. The need for protection of the myocardium during ischemic arrest has been well recognized and a number of methods including local and systemic hypothermia, intermittent coronary perfusion, retrograde coronary perfusion with cold blood, coronary perfusion with cold lactated Ringer's solution, tetrodoxin, acetylcholine, chemical asanguinous K+ cardioplegia and cold blood cardioplegia, have all been used in experimental studies and clinical practice. Of these, hypothermia and pharmacological arrest with cold cardioplegic solutions have now gained wide acceptance in clinical practice, despite their causing vasoconstriction.

Hypothermia has been proved to be an effective method of myorcardia preservation. It provides a bloodless arrested heart, lowers the energy requirements, delays the depletion of high energy phosphate reserves and lactic acid accumulation, and retards the morphological and functional deterioration associated with ischemic arrest. The technique of topical cooling with continuous irrigation of the surface of the heart was first described in Surg. Gynaecol. Obst., 129:750 (1959). In this technique, the cooling proceeded from the surface of the heart to the interior and was unlikely to cool the subendocardium and the interventricular septum due to mediastinal and bronchial collateral return, which would warm the endocardial surface without profound hypothermia.

Moderate hypothermia and surface cooling have been generally found inadequate to protect the myocardium for more than one hour of ischemic arrest. On the other hand, deep hypothermia and surface cooling which have been sufficient of 90 minutes of ischemic arrest is known to cause myocardial damage due to crystallization of the membrane lipids and poor ventricular performance on perfusion. Canad. Anaesth. Soc. J., 27:381 (1980). Postgrad. Med. J., 59:11 (1983) reports that in addition to affording protection by reducing heart rate, hypothermia slows all metabolic processes (thus conserving energy) including damaging degradative mechanisms and pathways which produce toxic metabolites. The efficacy of hypothermia as a protective agent was reported as the post-ischemic recovery of function following a 60 minute period of ischemic arrest in the rat heart which is related to the degree of hypothermia during ischaemia. Reducing the myocardial temperature during ischaemia from 37° C. to 4° C. resulted in a progressive improvement of post-ischemic recovery from 0% to 96% of pre-ischemic function. The hypothermic protection is reported to be poor and falling off rapidly as the myocardial temperature rises above 28° C. In contrast, below 24° C. protection was excellent and was little improved with increasing degrees of hypothermia. The reason for the sharp inflection is unknown but might be related to lipoprotein phase transitions in cell membranes. If a similar relationship exists for the human heart, such results would strongly support the maintenance of myorcardial temperatures below 25° C. during periods of ischemic arrest. Since however, hypothermia causes constriction of the vessels, the blood remains in the vessels and leads to clotting and blockage of vessels.

In recent years, there has been considerable controversy over the extent to which hypothermia and chemical arrest are additive. And in a recent series of studies (Ibid.) in the rat and the dog, these effect have been clearly demonstrated. Dog hearts were subjected to 120 minutes of ischaemia at 20° C. In the hypothermia-alone group, non-cardioplegic solution was infused at 20° C. at the onset and after 60 minutes of ischaemia. In the hypothermia-plus-cardioplegia group, the infusion conditions were identical, with the exception that a high potassium-containing protective solution was used. Measurements of ventricular function before and after bypass revealed significantly better recoveries in the hypothermia-plus-cardioplegia group than in the hypothermia-alone group. Recoveries of cardiac output, left ventricular minute work and dP/dt in the hypothermia-plus-cardioplegia group were 92%, 62% and 91% respectively, whereas in the hypothermia-alone group the values were 38%, 17% and 43% respectively.

While the above used combination of cardioplegia with hypothermia was able to recover the cardiac function to about 92%, the time of ischaemia was limited to 120 minutes with the upper possible period of ischemic arrest around 4 hours.

In view of the above findings that (a) the moderate hypothermia above is inadequate to protect the myocardium for more than 1 hour; (b) profound cooling of myocardium causes myocardial damage; and (c) that combination of cardioplegia and mild hypothermia can only preserve the myocardial function for up to around 4 hours, it is clear that the technique which would be able to avoid deep hypothermia and still be able to preserve around 90% of normal function of myocardium after 24 hours ischemia would be extremely advantageous.

The principles of successful cardioplegic protection have been outlined (Ibid. p.11) as follows: energy conservation through the chemical induction of rapid and complete diastolic arrest; slowing of metabolic rate and degradative processes through the coincident use of hypothermia; and the prevention or reversal of certain unfavorable ischaemia-induced changes with various protective agents.

One of the means which was previously used to achieve almost immediate reduction in myocardial contractile activity is by aortic cross clamping. This reduction is however not complete and a reduced level of contractile activity is maintained sometimes for several minutes before the onset of diastolic arrest. This activity may also recur intermittently during the ischemic period. In addition to delaying a hampering surgical activity, this mechanical activity wastes substantial amounts of cellular energy. During myocardial ischaemia, ATP and creatine phosphate production is severely restricted. Those supplies which are available are used in an attempt to maintain cellular homeostasis such as, for example, transmembrane ion gradients and tissue protection. Needless depletion of these limited energy reserves by ischemic contraction can only hasten the process of cell death.

Other attempts to achieve rapid diastolic arrest were made by using various chemical means. Cardioplegic solutions were investigated containing high concentrations of potassium where coronary infusion of a solution containing 16 mmol potassium chloride/liter causes complete arrest within a few seconds. The effect of this upon myorcardial energy reserves and resistance to ischemia has been investigated in a study in which isolated rat hearts were subjected to a 2 minute period of coronary infusion with a cardioplegic (16 mmol potassium/liter) or a non-cardioplegic (5 mmol potassium/liter) solution immediately following aortic cross clamping. After 30 minutes of ischemia, the cardioplegic hearts contained 11.1±4.2 μmol of ATP/g dry weight and 9.4±2.1 μmol of creatine phosphate/g dry weight, whereas the corresponding figures in the non-cardioplegic group were 5.3±0.9 and 2.8±0.4 μmol/g dry weight respectively. This striking difference in high energy phosphates was reflected in the post-ischemic recovery of function, which was zero in the non-cardioplegic group as opposed to almost 50% in the cardioplegic group.

Potassium is not unique in its ability to induce cardiac arrest. Numerous other agents have been used clinically and/or experimentally, for example zero calcium, high magnesium, acetylcholine, neostigmine and tetrodotoxin. In each instance, the primary protective effect has been through rapid induction of arrest and conservation of cellular energy supplies. In the light of current knowledge, however, some agents such as zero calcium or tetrodotoxin could not be recommended for clinical use, or in case of transplantation of the heart.

Thus it would be desirable to be able to achieve the rapid diastolic arrest without using undesirable agents.

Successful preservation of the heart for transplantation depends on maintenance or restoration of the full myocardial contractility.

Numerous attempts have been made to improve the biochemical properties of cardioplegic solutions and to optimize myocardial protection during the extreme form of ischemia. This attempts are described in *Biomed. Biochim. Acta.*, 46:499 (1987); *Circulation.* 76:180 (1987); *J. Suro. Res.*, 42:247 (1987); *Clin. Physiol.*, 7:43 (1987); and *Cardiovasc. Surg.*, 91:259 (1986).

The most commonly used cardioplegia is crystalloid cardioplegia consisting of isotonic or slightly hypertonic saline supplemented with glucose and potassium chloride of which buffering capacity is usually afforded by the addition of sodium bicarbonate or THAM. In addition, some solutions contain small amounts of magnesium or calcium, glucose, ATP, creatine phosphate while others contain pharmacologic agents such as mannitol, insulin, procaine or calcium channel blockers. Blood cardioplegia is also investigated but was not better than the other cardioplegia.

Despite these advances in cardioplegia, a significant percentage of patients continue to demonstrate clinical evidence of myocardial damage in the postoperative period *(New Engl. J. Med.*, 301:135 (1979), indicating that the current cardioplegia is not suitable for purposes of the heart preservation for transplantations for longer period of time.

For preservation of cellular mitochondrial function, it is important to arrest the heart immediately since significant utilization of high energy phosphates occurs during the brief period of contractile activity between the onset of ischemia and the onset of asystole. *J. Thorac. Cardiovasc. Surg.*, 77:803 (1979); *J. Surg. Res.*, 24:201 (1978). This is particularly important since myocardial recovery from prolonged global ischemic arrest depends in part on the conservation of high energy phosphate stores, on the presence of the substrate in the cardioplegic solution and on the avoidance of reperfusion injury at the cellular level. No substrate present, ischemia occurs, when the glucose is used as the substrate, edema develops. *J. Mol. Cell. Cardiol.*, 13:941 (1981).

Decrease in cardiac performance due to insufficient supply of free energy is well documented. A reduction in contractile performance of isolated hamster heart correlates with a decrease in free energy of ATP hydrolysis. *Cardiac Adaptation to Hemodynamic Overload, Training and Stress.*, 197 (1983) Ed. R. Jacob et al., Steinkopff Verlag.

When the glucose was used as a sole substrate edema developed and the high energy phosphates ATP and phosphocreatine reached maximum values during heart diastole and minimum during systole. Upon exhaustion of ATP, a decrease in high level phosphate accompanied by a low level in the free energy of ATP hydrolysis, augmented levels of lactate and inorganic phosphate resulted in a 50% reduction of cardiac performance. *Cir. Res.*, 53:759 (1983).

Since during the myocardial contraction the high level energy is required, and since in particular in the heart removed from the donor for the transplantation the supply of nutrients is limited to those present in the cardioplegia, and since glucose which is currently used as the energy supply, metabolizes in the muscle cells to lactate, the myocardial tissue soon faces a metabolic acidosis. Also, there may be an incomplete breakdown of glucose in cells resulting in lower than 6 carbon sugar or phosphorylated sugar which may cause intracellular ionic inequilibrium which causes water to be retained intracellularly with edema. Under high work-load conditions with glucose as a sole substrate, glycolytic production of pyruvate is inadequate to meet the energy needs under aerobic or anaerobic conditions, and consequently the acidosis develops. The acidosis, particulary combined with cellular edema in turn may cause a number of detrimental effects on cardiac function during myocardial ischemia including electrophysiological abnormalities and a reduction in ventricular performance, gradual decrease in tension, and decrease in coronary flow. The metabolic depletion of ATP impairs the post ischemic recovery of myocardial performance.

If glycolysis is rate limiting, there is reduced delivery of pyruvate to the mitochondria. By substituting pyruvate for glucose glycolysis is bypassed and pyruvate is available to the mitochondria for oxidative phosphorylation producing free energy ATP. *Ann. J. Physiol.*, 253: H 1261 (1987). The use of pyruvate as a sole exogenous substrate results in greater functional and biochemical recovery after 30 minutes of ischemia and 30 minutes of reflow.

*Circ. Res.*, 35:448 (1974) reports that intracellular $Ca^{2+}$-overload, the major factor contributing to myocardial injury during global ischemia in reperfusion, leads to impaired oxidative phosphorylation, increased ATP breakdown and consequently inefficient ATP utilization for mechanical work. Many studies document the usefulness of a calcium antagonist as adjuncts to cardioplegia in order to prevent intracellular $Ca^{2+}$ accumulation and its deleterious effects *Ann. Thorac. Surg.*, 42:593 (1986), *Am. Heart J.*, 118:1219 (1989).

Using the currently available cardioplegic solutions, the safe time of global myocardial ischemia in human hearts is limited to 120 minutes. As reported in *Heart Disease*, 1962 (1988), 3rd Ed., Harcourt Brace Jovanovich, within this period no significant myocardial necrosis or permanent functional damage results. Under these conditions, *Principles in Surgery*, 407 (1984) 4th Ed., McGraw Hill, suggest that hearts for transplantation in humans must be implanted within 4 hours from the time of the heart removal.

Therefore, it would be advantageous for a worldwide transplantation network to extend this time period to possibly 24 hours or more. With the transportation feasibility to connect around the world in 24 hours, a supply of the hearts for transplantation could be widely improved and made practical if these hearts were able to be fully functional after 24 hours.

It has been previously reported, that the heart is severely affected by ingestion of large amounts of alcohol. Changes such as impaired sodium, potassium stimulated ATPase activity, inhibition of sodium-calcium exchange, decreased fatty acid oxidation, depressed ATP, impairment of mitochondrial function and diminished ratios of phosphate to oxygen all lead to a reduction in cardiac contractility. While higher alcohol concentrations produce a sudden cardiac arrest in the isolated hamster and rat heart, acute alcohol exposure reversibly depresses cardiac function without affecting energy resources. *FASEB. J.*, 2:256 (1988) and *Mag. Res. in Med.*, 8:58 (1988) reported that perfusion of the isolated hamster heart with 2% ethanol for 30 minutes, showed decrease in developed pressure, a marked increase in end-diastolic pressure, a decrease in ATP and an increase in inorganic phosphate and prevented a cellular edema. There was no change in phosphocreatine or intracellular pH. After reequilibration, all the above values returned to almost normal levels showing that alcohol induced functional cardiac depression is reversible.

It is a primary object of this invention to provide an improved technology for long-time preservation of the heart for transplantation by using novel cardioplegic solutions and process of using these solutions to achieve the almost complete functional myocardial contractility restoration after 24 hours ischemia.

SUMMARY

One aspect of this invention is a novel and improved process for long-term preservation of the heart for transplantation.

Other aspect of this invention is the preservation of the heart for period 24 hours or longer wherein at that time the heart recovers 90-100% of its original contractile activity and around 70% of its mitochondrial activity.

Another aspect of this invention is preservation of the heart by sequence of events including a perfusion, at a warm temperature of the heart with the first cardioplegic solution which contains pyruvate in order to remove the blood from the heart atriums and ventricles and to load the cells with pyruvate, followed by the perfusion of the heart with the second cardioplegic solution containing pyruvate and ethanol in order to achieve a rapid arrest of cardiac activity, to stop metabolic processes and bring the metabolism to a basal rate and to prevent a development of cellular edema, and preserving the heart aseptically in the large volume of the first solution for 24 hours or longer at temperatures between 4°-10° C.

Still another aspect of this invention is the first novel cardioplegic solution containing ions sodium chloride, potassium chloride, calcium chloride, sodium bicarbonate, sodium EDTA, magnesium chloride in admixture with sodium pyruvate and a protein.

Yet another aspect of this invention is the second cardioplegic solution comprising the first cardioplegic solution with additionally added ethanol.

Still another aspect of this invention is the prevention of development of metabolic acidosis and edema in the myocardial cells by using the pyruvate to provide energy supply but to eliminate the acidic metabolite lactate or products of incomplete breakdown of glucose formed during the previously used glucose as an energy supply.

Still yet another aspect of this invention is the cardiac arrest achieved by the perfusion of heart with the second cardioplegic solution, which results in a rapid and almost complete cardiac arrest due to the presence of alcohol in the second cardioplegic solution and wherein such cardiac arrest is reversible after periods of storing in the first solution for as long as 24 hours with the recovery of the myocardial contractility being at that time around 90% of the original activity.

DETAILED DESCRIPTION OF THE INVENTION

Figure 1A:
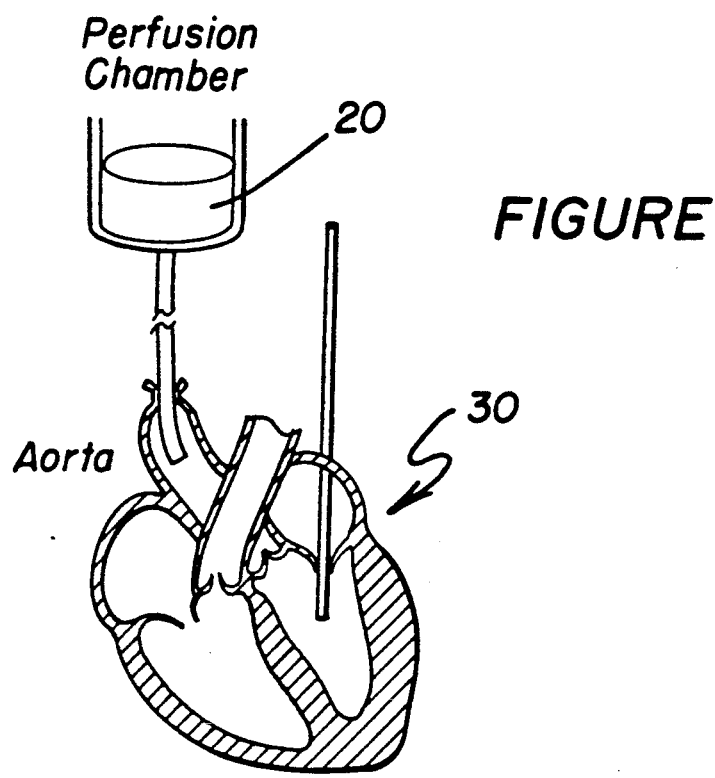
FIG. 1 is a diagrammatic representation of cardioplegic conditions.

This invention concerns a novel and improved process for long-term preservation of the heart for transplantation. The preservation process comprises the following:

1. The heart is perfused at a warm temperature with a physiological solution containing pyruvate to vasodilate, remove blood, increase flow, and load the cells with an energy supply in the form of a clean substrate, namely pyruvate. Pyruvate prevents edema, ischemia, calcium overload, and acidosis. It also helps preserve the active potential across the membrane.

2. Cannulation of the aorta, pulmonary outflow tract, and left ventricular chamber allows for a more complete exchange of gas, substrate, and media during perfusion and storage, thus allowing for usage of pyruvate as an energy source.

3. Perfusion with a second solution (cardioplegic) containing both pyruvate and alcohol stops the heart from working (cross-bridge turnover), vasodilates vessels allowing for full vascular flow, continues to load the cells with pyruvate, and preserves the energy state of the heart.

4. Storage of the heart, via specific techniques, allows the heart to remain in a closed aseptic container for transfer, permitting diffusion of gases and media during the interim of 24 hour transfer, retaining the heart in a healthy viable state. Unlike other cardioplegic solutions no edema, calcium loading, vasoconstriction or ischemia occurs.

A novel technology for long-term preservation of the heart for transplantation has been developed. The technology comprises of two novel cardioplegic solution and the sequential process of using these two solution to achieve the heart preservation for periods of 24 hours or longer after which time the heart recovers 90-100% of its normal activity and around 70% of its mitochondrial activity. Until now no technology or cardioplegic solution has been available to preserve hearts for such long periods of time. This technology is in particular useful for easy transportation of the heart without special requirements for unusual equipment such as refrigeration or freezing chambers and such transportation may be made in any type or kind of container which allows aseptic conditions, maintenance of temperature of 4°-10° C. for 24 hours or longer, as needs be, and a slow influx of oxygen during the preservation period. For extended period of time over 24 hours, the cardioplegic solutions medium contains additional nutrients enabling the basal metabolism to proceed to assure the heart recoverability at the end of preservation period and before a transplantation.

The unique properties of the process are (a) perfusing the heart with a first novel cardioplegic solution containing a pyruvate, fetal calf serum and EDTA, at a warm, preferably room temperature to remove blood and metabolites from the heart and to increase the coronary flow of the perfusate; (b) serially perfusing the heart with a second nove cardioplegic solution comprising the first solution and alcohol, preferably ethanol, to bring about the reversible cardiac arrest and decrease in metabolism to the basal metabolic rate, said perfusion being performed at a between 4° C.-37° C. temperature; and (c) submerging the heart having cannulated aorta and left ventricular chamber to allow for diffusion of gases substrate and cardioplegic media, into the large volume of the first solution for entire preservation period. The preservation step is maintained at temperature between 4°-10° C. for the entire period of the heart preservation.

Unique properties of the cardioplegic solutions are: (a) a presence of pyruvate as a substrate for energy supply demands substituting for generally used glucose which leads to the metabolic acidity and edema causing the damage to myocardial cell and impairment of the heart function; (b) a presence of a protein albumin or fetal calf serum useful for tissue renewal; (c) low or none phosphate to pressure energy; (d) a presence of Ethylenediaminetetraacetic acid (EDTA) used for removal of harmful ions; and (e) in case of the second cardioplegic solution, the presence of ethanol to affect a reversible cardiac arrest and vasidilation.

The combination of novel process using novel cardioplegic solutions results in unique technology for preservation of the heart for transplantation for periods six or more time longer than known until now.

Design of Cardioplegic Solutions

Successful cardioplegic solution suitable for long-term preservation of the heart must protect the heart against deleterious effects of the long-term induced myocardial ischemia which results from the interrupted oxygen supply during the time when the circulation of the donor is stopped before or during the heart removal from the donor and until the heart is connected in the recipient's circulation which assumes the oxygen-blood supply. Since it is well known that the myocardial ischemia extended over 20-30 minutes has often fatal consequences due to irreversible damage to the heart, it is necessary to design either the cardioplegic solution in such a way that it would prevent ischemia to occur or to design a conditions which would allow ischemia to occur but would still assure that there is no irreversible damage to the heart and that, after the ischemic period, the heart can resume its contractile activity.

In designing the novel cardioplegic solution of this invention, ions are needed to retain the potential difference across the membrane but must be chosen carefully. Some inorganic phosphate (Pi) is needed, too much lowers the energy state. Some $Ca^{2+}$ is needed, but too much results in increased work. Some $Mg^{2+}$ is needed, but too much competes with $Ca^{2+}$. Some KCl is needed but when too much is present, the vascular system is constricted. Bicarbonate is needed to retain the pH in a physiological state. Sodium chloride is used to balance the osmolarity and retain the potential difference across the membranes.

As has been discussed above, while the source of energy for the continuous, even basal metabolic state, heart activity is necessary, it has been found that glucose, which was until now predominantly used as a source of energy in currently available cardioplegic solutions causes the acidosis and edema of the tissue which subsequently results in the impairment of the contractile function of the myocardial tissue. Glucose and fatty acids are more deleterious to the heart during ischemia due to build up of by-products, including accumulation of sugar phosphates. Pyruvate is a beneficial substrate protecting the heart against ischemia, acidosis, and a calcium overload and does not cause cellular edema. These fundamental observations led to formulation of a saline solution with pyruvate as the substrate and to the current finding that by substituting glucose in the cardioplegic solution with pyruvate, the tissue acidosis and edema does not occur and when combined with alcohol as an agent to arrest the heart activity, a beneficial cardioplegic solution suitable for long-term preservation of the heart results. The discovery described here indicates that the cardioplegic solution containing pyruvate, and especially pyruvate plus ethanol protects the heart against a 24 hour period of cardioplegia.

In the absence of work the heart is able to survive in and utilize a basal energy rate because there is an excess concentration of high energy phosphate present in the heart. It appears that when the heart is in a cardioplegic state there is sufficient diffusion of oxygen in the media to maintain the basal energy state of the heart. This occurs at a reduced energy level, but substrate may be necessary to maintain a viable basal rate. Consequently, when the suitable substrate, such as pyruvate, is provided and when the heart is introduced into the basal energy rate by the alcohol, the heart is able to survive without substantial damage and impairment of its contractile function for at least 24 hours or longer.

Advantages provided by this invention became readily apparent, since the previously known survival of the heart of ischemia induced by the removal of the heart from the donor was only somewhere around 2-4 hours, at which time the heart needed to be placed in the recipient circulation, or the irreversible damage or death of the heart occurred.

Basic cardioplegic solution of this invention is based on finding that ions are needed to retain the cell potential difference across the membrane but must be chosen carefully. While some inorganic phosphate (Pi) is needed, too much of Pi lowers the energy state, while some calcium ($Ca^{2+}$) is need, too much results in increased work. Some magnesium ($Mg^{2+}$) is needed, but too much competes with $Ca^{2+}$. When too much of KCl is added, the vasoconstriction results. Bicarbonate is needed to retain the pH in a physiological state. Sodium chloride is used to balance the osmolarity and retain the potential difference across the membranes.

The cardioplegic solution of this invention contains, per liter or deionized distilled sterile water, 90-120, preferably 17 mM (6.25 g) of sodium chloride, 4.0-4.5, preferably 4.3 mM (0.320 g) of potassium chloride, 0.5-2.5, preferably 2 mM (0.294 g) of calcium chloride, 22-28, preferably 25 mM (2.1 g) of sodium bicarbonate, 0-1 mM, preferably 0.5 mM (0.146 g) of ethylenediaminetetraacetic acid (EDTA), 1.0-2.0, preferably 1.2 mM (0.144 g) of magnesium sulfate or equivalent amount of magnesium chloride, 6-12, preferably 10 mM (1.1 g) of sodium pyruvate, and 0.05-1%, preferably 0.1% of protein such as fetal calf serum, serum albumin such as synthetic or natural albumin or any other protein which will provide viscosity similar to the albumin.

Solution 2 consists essentially of the solution 1 with added 2-8%, preferably 4% of lower alcohol, such as ethanol and may be used at temperatures from 4° C.-37° C. In alternative, alcohol may be substituted with additional 18-26 mM, preferably with 20 mM (1.3 g) of potassium chloride which can only be used at temperatures between 2°-8° C.

Both solutions may contain additionally 5-20% of fluorocarbon, such as perfluorocarbon obtained from Green Cross, Japan which is emulsified.

In another embodiment, the cardioplegic solutions may additionally contain individual essential amino acids or mixtures thereof, or be completely substituted with Eagle or 199 media obtained, for example, from Gibco Laboratories.

Procedure for Heart Preservation

Figure 1B:
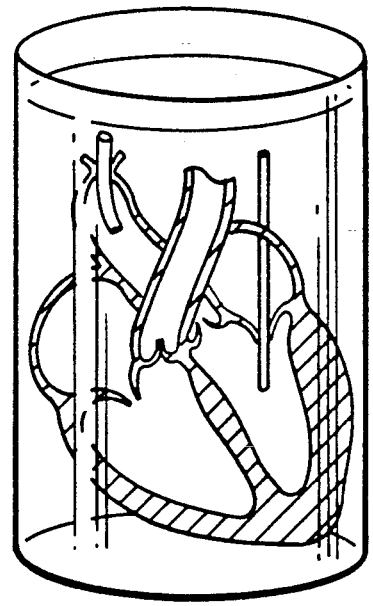
Figure 1C:
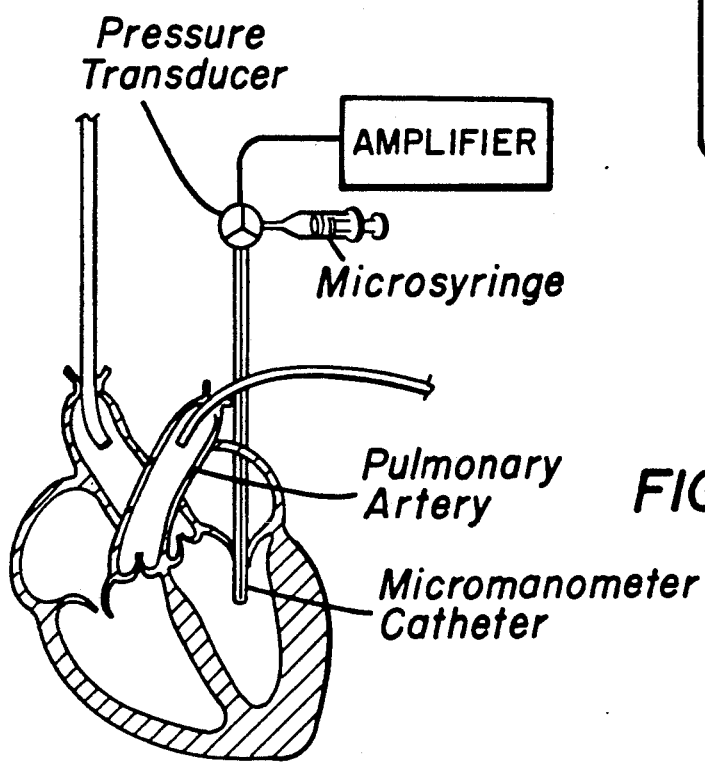

Heart 30 with cannulated aorta, pulmonary artery and with introduced micromanometer catheter in the left ventricle as shown in FIG. 1C is connected to the perfusion chamber 20 connected to container 40 containing solution 1 and container 50 containing solution 2, both being regulated with valves 42 and 52 respectively. Each container has build-in thermister to enable to preset and maintain certain temperature. Perfusion by the solution 1 or 2 then proceeds the perfusion with solution 1 containing pyruvate which bypasses the glycolytic pathway. Glycolysis is slow in the heart, especially in the cardio-myopathic heart. Glycolysis is partially rate-limited by phosphofructokinase, which is inhibited by intracellular calcium $[Ca^{2+}]i$ and hydrogen ions $[H^+]i$ and activated by cAMP. $[H^+]i$ and $[Ca^{2+}]i$ are augmented in cardiomyopathy. When glucose was used as the only substrate, in the cardioplegic solution [NADH]/[NAD], the phosphorylation potential and developed pressure were significantly lower and concentrations of phosphomonoester sugars and hydrogen ions $[H^+]i$ were significantly higher in isolated cardiomyopathic hearts as compared to healthy hamster hearts. Pyruvate on the other hand was shown to lower diastolic $[Ca^{2+}]i$ decreased significantly in myopathic hamster hearts. The results published in *Basic Res. Cardial.*, (1990), suggest that heart failure is partially the result of calcium and/or hydrogen ion induced inhibition of glycolysis, which is alleviated by bypassing the glycolytic pathway with pyruvate.

Consequently, the presence of pyruvate in the solution provides unique protection for the heart cells by preventing development of edema, ischemia, calcium overload, acidosis and preserve the cell membrane potential across the membrane.

The heart is perfused with solution 1 for 1-20 minutes, preferably for about 10 minutes at a warm temperature between 28° C. to 37° C., preferably around 35°-36° C. At this temperature, the solution vasodilates the heart vessels, as opposite to the cold cardioplegia which causes vasoconstriction of the heart, increases flow and loads the cells with an energy supply in the form of a clean substrate pyruvate.

Cannulation of the aorta and pulmonary artery allows the solution to circulate through the whole heart and thus provide exchange by diffusion of gas, substrate and media during perfusion and storage between the solution and the cells. At the end of perfusion with solution 1, the value 42 is closed and the value 52 is opened to allow perfusion with solution 2 containing alcohol. Solution 2 containing both pyruvate and 2-6% of alcohol, preferably 4% of ethanol, causes the arrest of the heart contraction by inhibition cross-bridge turnover, vasodilation and also inhibits the $Na^+/Ca^{2+}$ exchange by preventing the efflux of $Ca^{2+}$. A combination of low $Na^+$ and ethanol lowers the influx of $Na^+$ during the calcium paradox and the efflux of $Ca^{2+}$ as shown here. As a result the cell is not depleted of $Ca^{2+}$ during the calcium paradox and not loaded with $Ca^{2+}$ during repletion and the heart is able to recover from the calcium paradox during reperfusion when ethanol is present during the $Ca^{2+}$-depletion period. To assure a low $Ca^{2+}$ concentration during the $Ca^{2+}$-depletion period, 0.5 mM EDTA was added to the perfusate.

Perfusion with the second solution containing alcohol proceeds for 1-20 minutes, preferably around 10 minutes at temperatures from 2° C. to 37° C. Higher temperatures than 28° C. are preferred because they allow for vasodilation but when the circumstances require, the temperature may be lowered to about 4° C. which will further slow down metabolism but more importantly will cause certain degree of vasoconstriction. The perfusion with the cold solution containing potassium chloride is preferably done at low temperatures around 4° C.

In alternative, the heart preservation according to the procedure of this invention can be successfully accomplished by perfusion with solution 1 at warm temperatures (24°-37° C.) and by subsequent cooling of the solution 1 to temperatures between 2°-10° C., preferably to 4° C. This temperature is also used for the storage period for this procedure wherein the heart cannulated with cannulae intact is transferred to the container depicted in FIG. 1b. The only requirements for the container are that is tightly closed, filled with enough of solution 1 in such quantity, usually between 3-8 liters, which allows complete submerging of the heart with cannulae in the solution, that the aseptic conditions can be preserved including the aseptic supply of gas, preferably oxygen/carbon dioxide 95/5%, and the temperature is maintained around 4° C. In alternative, the container may be equipped with the perfusion pump and the heart may be continuously perfused with solution 1 at temperature between 2°-8° C., preferably around 4° C.

Using the procedure of this invention, the heart may be successfully preserved from 24 hours to seven or more days provided that the constant supply of oxygen and essential energy substrate and nutrients is provided.

Additional agents, such as drugs, hormones, vitamins and other pharmaceutically acceptable excipients may be added to solution 1 or 2.

The feasibility of the cardioplegic solutions for long-term heart preservation was studied on animal hearts. Isolated hamster or rat hearts were first perfused with a normal Krebs-Henseleit or Langeidorf medium to demonstrate comparable viability of hearts prior to perfusing and storing for 24 hours in one of three solutions. The three solutions applied to three groups of hears are described in Example 1 and were: Solution (A) a physiological saline containing pyruvate as the substrate and 4% alcohol to arrest the heart; Solution (B) a standard cardioplegic solution; and Solution (C) a physiological saline containing pyruvate as the substrate. The procedure was a described in Example 2.

The results are summarized in Tables I and II.

Figure 3A:
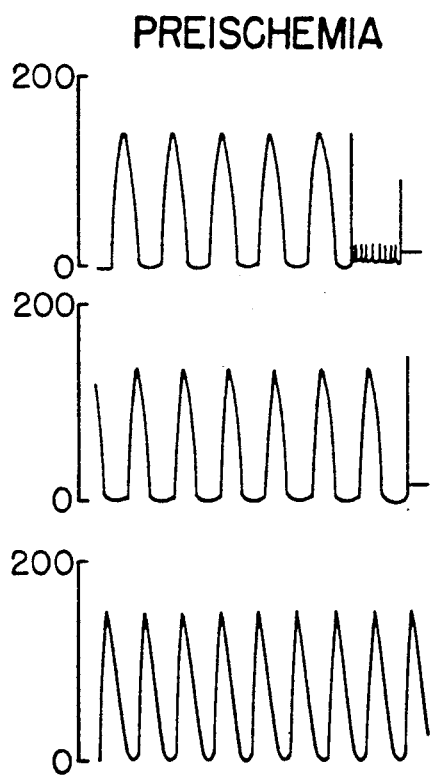
FIG. 3 depicts ventricular pressure for hearts perfused by cardioplegic solutions in pre-ischemic and post-ischemic hearts.
Figure 3B:
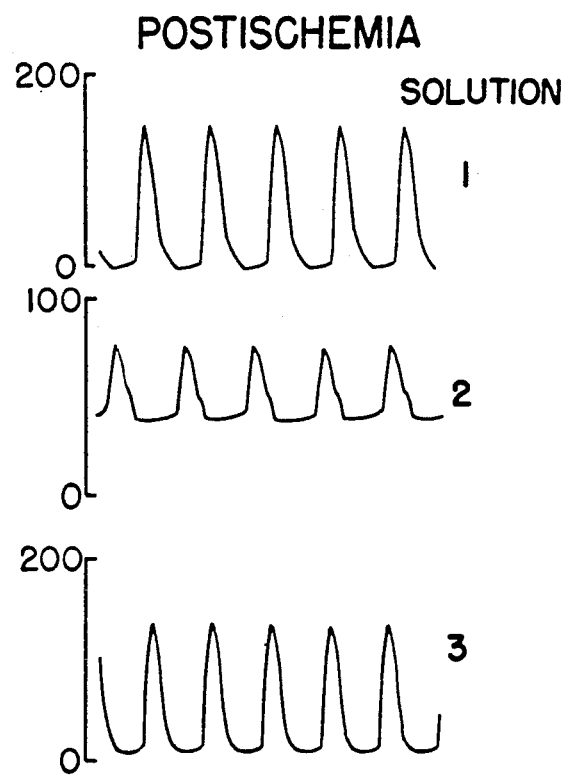

FIG. 3 shows a representative drawings of left ventricular pressure for hearts perfused in solutions A, B and C for baseline levels, called preischemia, and 30 minutes reperfusion following 24 hours of storage called postischemia in each solution A at 4° C. For solution A, which includes pyruvate and 5% of ethanol, the preischemic and postischemic pressure is almost the same, i.e., the height of peaks is the same and only the rate of the contractions in postischemic heart in solution is slower. Thus, this solution is able to preserve the pressure and the heart for 24 hours without any apparent impairment in cardiac function. This coincides with results summarized in Table I where the developed pressure and end-diastolic pressures are the same for pre- and post ischemia. Coronary flow and heart rate are somehow slower and the oxygen consumption is about the same. For solution C, containing pyruvate as a substrate results are similar. Although the height of the developed pressure is postischemia is not quite the same as in preischemia, during the contractions of the heart, the pressure returns to 0 levels. Both end diastolic pressure and coronary flow are the same with heart rate slower and oxygen consumption slightly lower in post-ischemia. Solution B which has no pyruvate and no alcohol, shows drastical reduction in heart contractility, wherein the postischemic heart contracts only somewhere between 40–70 mm Hg instead of 0–160 as seen in preischemic heart. The results in Table I support these findings. Developed pressure, coronary flow, heart rate and oxygen consumption are all much lower, with end diastolic pressure much higher. This confirms that the heart stored in solution, B is edemic and ischemic, probably due to too much of $Ca^{2+}$, and lack of available energy substrate, and its function is only about 50%.

Figure 4A:
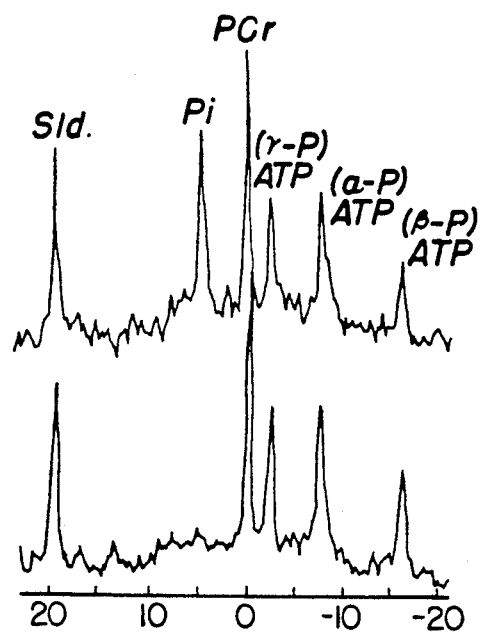
FIG. 4 depicts NMR spectra of hearts pre-ischemic and post-ischemic baseline energy level.
Figure 4B:
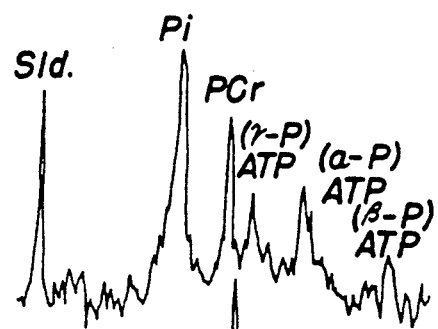
Figure 4C:
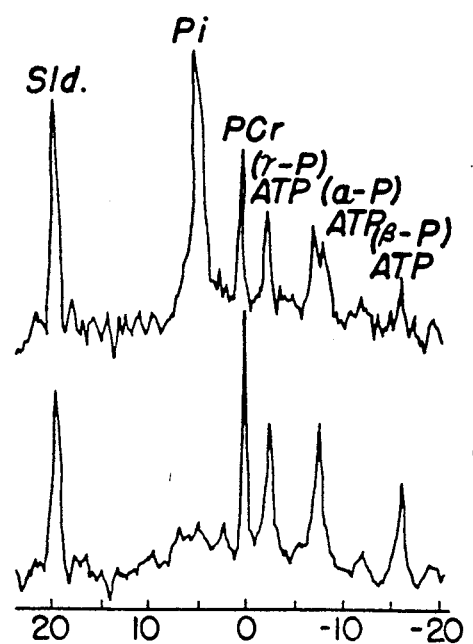

FIG. 4 A, B and C shows representative 31P-NMR spectra of hearts preischemic (baseline energy level) and postischemic (30 min reperfusion following 24 hours storage) for hearts perfused in solution (A), solution (B), and solution (C).

The upper lower spectra show the preischemic spectra, the upper spectra are postischemic. When the energy level is about the same, the spectra look the same. As seen from Spectra A, both upper and lower spectra are about identical, while spectra B, showing the energy level after 24 hours storage in Roe Standard solution, shows the presence of large amount of inorganic phosphate evidencing intracellular inequilibrium and intracellular acidity. ATP and creatinephosphate (PCr) are grossly diminished when the solution C was used without alcohol, depletion in energy supply is also seen because the heart was not put into the basal metabolic rate state and there was not sufficient supply of energy substrate to support full heart metabolism. The spectra in FIG. 4 are confirmed by results summarized in Table II.

In practice of this invention, the donor's heart aorta and the left ventricle are first cannulated for making hemodynamic measurements of baseline levels (preischemia) at a 140 cm $H_2O$ for storage. The heart is then excised and placed in the perfused working heart apparatus (FIG. 2) and the perfusion with the first cardioplegic solution is started through the cannula connected to container containing Solution 1 immediately. The perfusion continue for 2 to 60 minutes, preferably for about 5–10 minutes or until all remnants of the blood are washed out from the heart atriums and ventricles. When the rinsate is clear of blood, the cannular connection is switched to the container 2 containing cardioplegic solution 2 containing about 4% of ethanol. Both containers are kept at temperature between a room temperature to around 45° C., preferably at temperature allowing the perfusing solution 1 or 2 to have a body temperature of about 37° C., with option that solution 2 may have lower temperatures even around 2° C. Thus, perfusion with colder temperatures as low as 2°, preferably 4° C. is possible and contemplated to the within the scope of this invention.

The controversy of the applied temperature of a cardioplegic solution has been discussed above. Although the most commonly used cardioplegic solution is a cold potassium chloride solution, advantages of warm, oxygenated blood solution were described in J. Thorac. Cardiovasc. Surg., 91:888 (1986). Perfusing the heart with solutions at warm temperature was found beneficial in order to flush the coronaries and prevent them from collapsing. It was found to be important to remove all blood from the heart since the breakdown of hemoglobin releases, among other things, iron which may have deleterious effects on clotting and inhibition of enzymes.

The perfusion of the heart with the solution 2 effectively stops the heart work and induces the basal energy state. At this state in which the heart is in the basal rate state, as evidenced by the diminished or disappearance of the contractions of the heart as measured by ECG, the heart still with both cannulas intact and opened is transferred to the storage container filled with solution 1 and maintained at temperature between 4° C.–10° C., preferably about 8° C. Container can be of any size and shape as long as it may contain at least 4–8 liters of solution 1 so that the cannulated heart including open ends of cannulae are submerged at all times in the solution 1. One example of such container is shown in FIG. 1(b). It is important that the container is tightly capped and is equipped to provide slow but continuous influx of oxygen. The container and a solution therein must both be sterile and the influx of oxygen must be done aseptically. The cannulation tubes are provided and are necessary for continuous aeration by diffusion of the coronaries, atriums and ventricles, in particular the left ventricle while in the storage container. The cannulation tubes are designed so that the physician performing transplantation can connect the left ventricular cannula to a pressure transducer in order to check pressure before transplanting.

Tightly closed container is connected to a transportable miniature oxygen supply and is transported and transportable anywhere in the whole world by means of transportation, and as long as it is not submitted to excessive heat or cold which would damage the heart tissue, it can be stored for at least 24 hours or more and transplanted without loss of function. Following the properly done transplantation the isolated heart for transplantation will regain 90–100% of its normal physiological function and around the 70% of its mitochondrial activity immediately upon connecting the heart to the recipient's circulation and can survive in the cardioplegic solution of this invention from 24 hours to 7 days.

Surgical techniques may need to be altered in order to prevent CNS dysfunction during reperfusion of the implanted donor heart containing the 4% ethanol or the preserved hearts would need to be reperfused in a solution containing pyruvate prior to implanting, in order to remove ethanol.

Consequently, alcohol as a cardioplegic solution may have limited use for implantation unless the alcohol is perfused out of the system prior to use. Thus, it is contemplated to be advantageous to store the heart in the physiological saline containing pyruvate but not alcohol. Functional recovery in the latter is better than a standard cardioplegic solution.

UTILITY

This invention is useful for organ transplantation, in particular for the heart transplantation which requires, beside suitable cardioplegic solution, also special conditions in order to preserve its physiological function. The invention process is equally suitable for 24 hours preservation of the heart prior to the transplantation as it is suitable for longer than 24 hours preservation of the heart. In such an event, there will be continuous supply of oxygen pyruvate and/or other nutrients, ions and other agents needed for such extended survival. These extended preservation periods are within the scope of this invention. Various drugs and agents such as hormones, vitamins, nutrients, antibiotics and such others may be added to cardioplegic solution at any stage of the protective process of this invention as long as the aseptic conditions and safety are maintained.

The following examples are intended to illustrate the invention. They should not be in any way interpreted to limit the scope of this invention.

EXAMPLE 1

Preparation of Cardioplegic Solutions

This example illustrates preparation of cardioplegic solutions for long-term preservation of heart for transfusion.

Solution A 1.07 mM (6.25 g) of sodium chloride, 4.3 mM 320 mg) of potassium chloride, 2 mM (294 mg) of calcium chloride, 25 mM (2.1 g) of sodium bicarbonate, 0.5 mM (146 mg) of sodium EDTA, 1.2 mM (144 mg) of magnesium sulfate, 10 mM (1.1 g) of sodium pyruvate, 0.1% 1. of fetal calf serum and 4% of ethanol were dissolved at room temperature under constant stirring in 1 liter of deionized distilled sterile water, pH was adjusted to 7.4, and the solution was stored in the refrigerator at 4° C. until used for heart perfusion.

Solution B

20 MEq/l of potassium (K+), 27 MEq/l of sodium (Na+), 3 MEq/l of magnesium (Mg 2+), 47 MEq/l of chloride (Cl−) was dissolved in 1 liter of deionized water. The solution was adjusted to osmolarity 347 and pH 7.6 and stored at 4° C. in the refrigerator. The preparation of this solution is described in *J. Thorac. Cardiovasc. Surg.*, 73:366 (1977).

Solution C 1.07 mM (6.25 g) of sodium chloride, 4.3 mM (320 mg) of potassium chloride, 2.0 mM (294 mg) of calcium chloride, 1.2 mM (144 mg) of magnesium sulfate, 25 mM (2.1 g) of sodium bicarbonate, 0.5 mM 146 g) of Sodium EDTA and 10 mM (1.1 g) of sodium pyruvate were dissolved, under constant stirring in 1 liter of deionized water, pH was adjusted to 7.4, and the solution was stored at 4° C. in the refrigerator.

Before use, all solutions were oxygenated with mixture of 95/5% of oxygen/carbon dioxide.

EXAMPLE 2

Testing of Cardioplegic Solutions

This example illustrates testing and effect of cardioplegic solutions on the heart preservation.

Animal hearts were obtained from Golden hamsters weighing approximately 140 grams and 18 months of age. The animals were anesthetized with ether. After midline sternotomy the heart was rapidly excised with removal of the pericardium, immediately connected to an aortic perfusion cannula and perfused by a modified Langendorff method described in *Am. J. Physiol.*, 245:H 354 (1983) with a perfusion pressure of 140 cm $H_2O$. The oxygenated perfusate was equilibrated with 95% $O_2$ and 5% $CO_2$. All hearts were first perfused with a physiological saline [117 mM NaCl, 4.3 mM KCl, 2.0 mM $CaCl_2$, 1.2 mM $MgCl_2$, 0.1 mM $K_2HPO_4$, 25 mM $NaHCO_3$, 0.5 mM NaEDTA, 15 mM glucose, and 10 units/liter insulin.] After 15 minutes equilibration physiological measurements were made and energy metabolites were studied.

Physiological measurements included oxygen consumption, $pO_2$, and coronary flow. Oxygen consumption was determined as follows: Arterial samples were aspirated from the aortic chamber and venous samples were drawn from a catheter introduced into the right ventricular outflow tract for oxygen measurements (Corning model 165/2 gas analyzer). $PaO_2$ was measured and the oxygen content calculated as the product of coronary flow and coronary oxygen extraction. Coronary flow was determined by collecting the effluent of the right ventricle for one minute. A cannula was inserted through the left atrial appendage and into the left ventricular cavity, connected to a Statham P23Db pressure transducer.

Magnetic resonance spectroscopy was performed as follows. $31_p$ magnetic resonance spectroscopy of the beating isolated perfused heart was obtained on a 5.6 Tesla vertical 76 mm bore magnet as described in *Circ. Res.*, 59:597 (1986). $31_p$ NMR spectra were obtained without proton decoupling at 97.3 MHz, using a 1180 Nicolet computer, a pulse programmer, and a high resolution 20 mm broad-band probe. Pulse angle was 60° C., recycle time 1.25 sec, and spectra width 4000 Hz. The 512 transients were accumulated during a 10 minute period. The signal to noise ratio was approximately 30:1. To correct for partial saturation, fully relaxed spectra were obtained at 15 second recycle time, and correction factors for phosphocreatine (PCr) and intracellular phosphate (Pi) were determined (3% and 5% respectively). Chemical shifts are referred to the resonance position of PCr. The peaks characteristic peaks of intracellular phosphate, phosphocreatine and phosphate groups of adenosine triphosphate (ATP) were identified. Intracellular pH was standardized as follows: A standard solution at physiological ionic strength (150 mM KCl, 8 mM ATP, 10 mM PCr, 5 mM Pi, and 9 mM $MgSO_4$) was used at a temperature of 37° C. to obtain the chemical shift titration curve of pH dependent Pi to PCr peak difference; this curve was fitted to the Henderson-Hasselback equation. Phosphate peaks were quantitated using manual electronic planimetry and estimated for whole heart detection by comparison to a capillary tube of standard methylene diphosphonic acid fixed inside the NMR tube. High energy phosphate values determined by $^{31}$P-NMR were standardized by parallel studies of high pressure liquid chromatography of freeze-clamped tissue *Cardiovasc. Res.*, 20:471 (1986).

After the hearts were perfused with a Krebs-Henseleit solution physiological as well as biochemical measurements performed, the heart was transferred to solution 1, solution 2 or solution 3 as described in Example 1.

The hearts were perfused for 10 minutes with one of the three solutions. Then the cannula feeding the aorta was clamped, the cannulae leading to the aortic perfusate and to the pressure transducer were disconnected, and the heart submerged in one of the three respective solutions at 4° C. The details are depicted in FIG. 1. It was important that both cannulae were open during the 24 hours of storage for interchange with perfusate and dissolve $O_2$ in the perfusate. It was also important that no air entered the chamber during this time. After 24 hours of storage at 4° C., the cannulated hearts were again reperfused in a normal Krebs Henseleit medium. For reperfusion the cannula leading to the submerged aorta was clamped and placed in position of the perfusion apparatus. The cannula leading to the left ventricular chamber was again fastened into position.

The stimulator-triggered freeze clamp was attached to the perfusion apparatus. The pneumatic cylinders were driven at 60 Psi for "smashing" the heart and inducing a drop in temperature of the center of the heart from 37 37° C. to −80° C. within 5 msec. The frozen wafer fell from the anvils into liquid nitrogen when the cylinders were retracted using the neutralized extract, high energy phosphates were analyzed by high pressure liquid chromatography as described in detail in *IEEE Trans. Biomed. Eng.*, 29:448 (1982). The nucleotide were separated on a Beckman HPLC with a C-18 reverse phase column. All values were analyzed within a range of linearity.

Data are reported as mean and standard deviation. The unpaired Student t-Test was used for assessing the null hypothesis, and rejected at 95% confidence level.

EXAMPLE 3

Preischemic and Postischemic Cardiac Function

This example illustrates the preischemic and postischemic cardiac function depending on the cardioplegic solution used.

Three groups of isolated hamster hearts were perfused for 10 minutes with a Krebs-Henseleit solution according to procedures described in Example 2 and the base level (preischemia) of developed pressure expressed in mm HG measured in the left ventricle, end of diastolic pressure expressed in mm Hg, coronary flow expressed in ml/minute, heart rate expressed in beat/minute, rate pressure product $\times 10^3$ and oxygen consumption expressed in umoles/g/dry weight/minute was determined. Then, the hearts were perfused with one of the solutions listed in Example 1 as follows: Group I (6 hearts) was perfused with Solution A containing pyruvate and ethanol; Group II (6 hearts) was perfused with Solution B standard cardioplegic solution; and Group III (6 hearts) was perfused with Solution C containing pyruvate. The perfusion lasted about 10 minutes.

The hearts were then submerged for 24 hours in one of the three solutions described in Example 1. Both canulae were left open to assure the interchange with the perfusate solution and the supply of oxygen from the perfusate via cannulae into the heart. The ischemic period was 24 hours. After 24 hours of storage at 4° C., the cannulated hearts were again reperfused with a normal Krebs-Henseleit medium.

Preischemic, postischemic and control values were then determined and are summarized in Table I.

Figure 2:
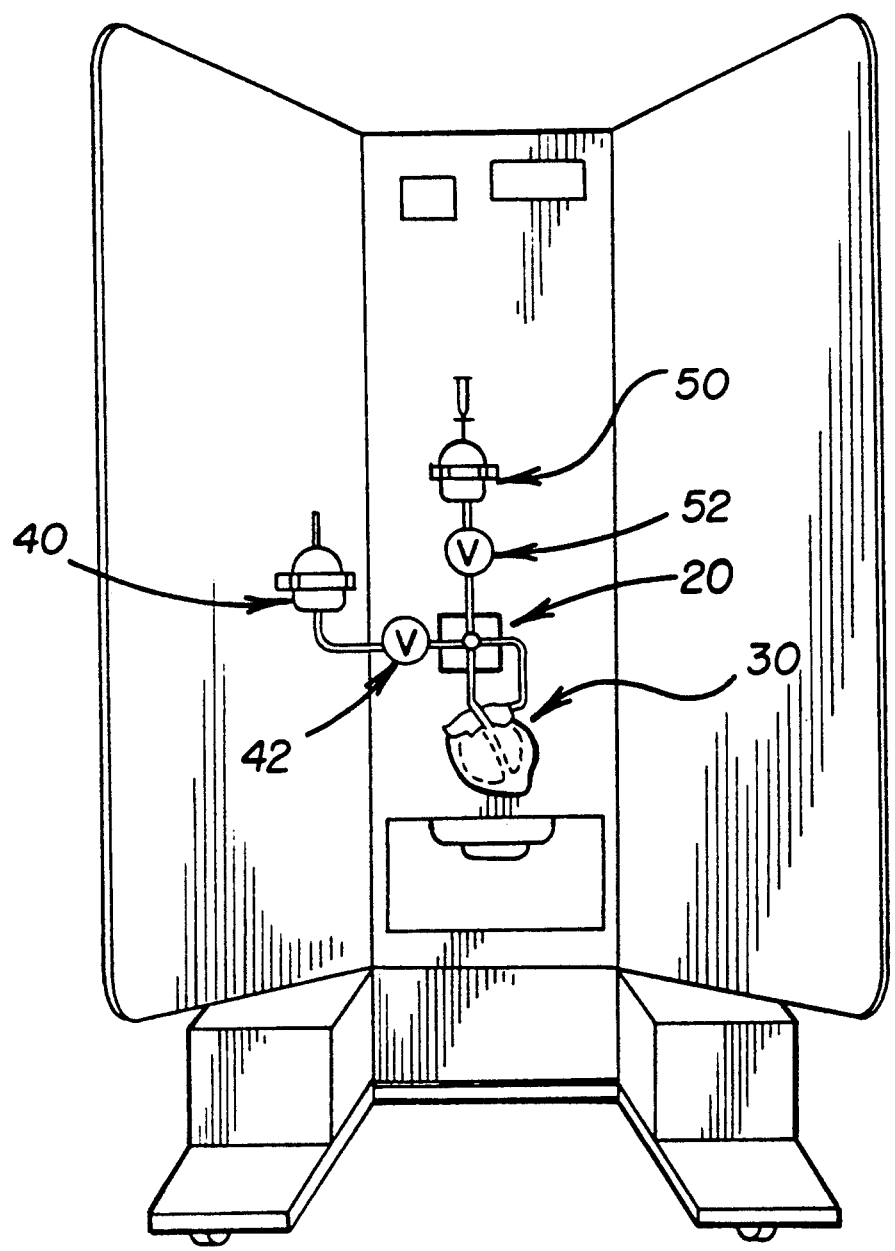
FIG. 2 is the model of isolated working heart apparatus.

Preischemic and postischemic cardiac function is shown in Table I for all three groups. Prior to ischemia, among all three groups there was no significant difference in developed pressure, end-diastolic pressure, coronary flow, heart rate and consumption prior to ischemia. In postischemia as compared to preischemia, Group I showed no significant difference in developed pressure, end-diastolic pressure and oxygen consumption, however, there was a small but significant ($p<0.05$) decrease in coronary flow, heart rate and the rate-pressure product. Group II, on the other hand, showed a significant ($p<0.01$) decrease in all measured hemodynamic parameters, except end-diastolic pressure; in latter there was a significant ($p<0.001$) increase in pressure. In Group III there was a significant ($p<0.01$) decrease in heart rate, rate-pressure-product, and $O_2$ consumption, but no significant change in developed pressure, coronary flow and end-diastolic pressure. Between Groups I and III, there was not significant difference in end-diastolic pressure, coronary flow, developed pressure and heart rate, postischemically, however the rate-pressure-product and $O_2$ consumption were moderately but significantly smaller ($p<0.05$) in Group III as compared to Group I. Group II postischemically had a significantly ($p<0.01$) lower developed pressure, coronary flow, rate-pressure-product and $O_2$ consumption as compared to Groups I and III, and a significantly ($p<0.001$) higher end-diastolic pressure. Representative tracing of left ventricular pressure for hearts perfused in Solution A, B, and C are shown in FIG. 2 for preischemia (baseline level) and after 30 minutes of reperfusion following the 24 hours of storage (postischemia).

Recovery, based on the rate-pressure-product and oxygen consumption after 30 minutes of reperfusion was 81% and 93%, respectively for Group I, 13% and 32% for Group II, and 70% and 72% for Group III. Percent of physiological recovery was not related to recovery of ATP.

Retention of the heart in a cold cardioplegic solution was necessary in order to maintain the basal energy state of the heart low. There was an interchange of metabolites and oxygen with the coronaries and ventricular chamber. If the heart was no cannulated, as described, the heart could only survive for a few hours. If the aortic cannula was clamped closed, survival time was 60-90 minutes. Cardiac function was better preserved in hearts perfused with a saline solution containing alcohol and pyruvate as compared to the standard cardioplegic solution.

TABLE I

| | I | II | III | IV | V | VI |
|---|---|---|---|---|---|---|
| GROUP I [N = 6] | | | | | | |
| (Modified Krebs-Henseleit Medium) | | | | | | |
| 5% Alcohol and Pyruvate as the substrate Solution A | | | | | | |
| Preischemia | 155 ± 16 | 2 ± 1 | 11 ± 1 | 218 ± 9 | 34 ± 2 | 39 ± 3 |
| Postischemia | 148 ± 13 | 2 ± 1 | 8 ± 2 | 184 ± 11 | 28 ± 2 | 37 ± 2 |
| GROUP II [N = 6] | | | | | | |
| Roe's Cardioplegic Solution B | | | | | | |
| Preischemia | 148 ± 12 | 2 ± 1 | 11 ± 1 | 215 ± 8 | 32 ± 1 | 38 ± 1 |
| Postischemia | 55 ± 11 | 65 ± 8 | 5 ± 2 | 150 ± 12 | 4 ± 1 | 12 ± 2 |
| GROUP III [N = 6] | | | | | | |
| (Modified Krebs Henseleit Medium) | | | | | | |
| Pyruvate as the substrate and no alcohol Solution C | | | | | | |
| Preischemia | 156 ± 9 | 2 ± 1 | 10 ± 1 | 210 ± 9 | 33 ± 1 | 35 ± 4 |

TABLE I-continued

|  | I | II | III | IV | V | VI |
|---|---|---|---|---|---|---|
| Postischemia | 134 ± 13 | 2 ± 1 | 10 ± 2 | 173 ± 12 | 23 ± 2 | 25 ± 3 |

I is developed pressure in mm Hg
II is end diastolic pressure mm Hg
III is coronary flow ml/min
IV is heart reate (BPM)
V is rate pressure product [×10³]
VI is Oxygen consumption u moles/g/day weight/min

EXAMPLE 4

Preischemic and Postischemic Energy Levels

This example illustrates the preischemic and postischemic energy levels depending in the cardioplegic solution used.

In the same three groups of isolated hamster hearts as described in Example 3, levels of ATP, phosphocreatine, inorganic phosphate [Pi] and intracellular pH $[pH]_2$ were determined. The results are summarized in Table II.

Preischemic and postischemic energy levels are shown in Table II. It was necessary to measure preischemic energy levels by $^{31}$P-NMR which is non-invasive so that the hearts would be available for further study. Standardized values obtained from $^{31}$P-NMR matched freeze clamped data. The NMR values were normalized and then standardized by parallel freeze clamped data. It was necessary to freeze-clamp in order to obtain the postischemic values since the energy levels were low at this time and difficult to detect by $^{31}$P-NMR in the small hamster hearts (approximately 0.6 grams). It was possible, however, to obtain the inorganic phosphate and $[pH]_i$ form the $^{31}$P-NMR data. The inorganic phosphate did not rise excessively high since there was no added phosphate in the perfusate. Preischemically there wa no significant difference in the energy metabolites among the three groups of animals, nor any difference in $[pH]i$. Postischemically there was no significant difference in ATP and $P_i$ among the three groups of animals (Table II). On the other hand, PCr was significantly higher in Groups 1 ($p<0.001$) and 3 ($p<0.01$) as compared to Group 2. There was no significant difference in $[pH]_i$ between Groups 1 and 3, however the $[pH]i$ was significantly more alkaline in Group 2 ($p<0.05$) (Table II). Representative $^{31}$P-NMR spectra are shown in FIG. 3 for baseline (preischemia) level and reperfusion following 24 hours of storage (postischemia) for hearts perfused and stored in Solution (A), Solution (B), and Solution (C).

The ATP level returned to approximately 40% of control level in all three groups, and in all three groups inorganic phosphate remained approximately 320% over control level after 30 minutes of reperfusion. Phosphocreatine was significantly higher in Groups 1 and 3 as compared to Group 2, related to improved oxygen consumption. Intracellular pH (pH)i, based on $^{31}$P-NMR, was physiological in Groups 1 and 3 but alkaline in Group 2. The latter may have been due to leaky membranes. Pyruvate helped to preserve mitochondrial function during depressed oxygen delivery, i.e., during 24 hours storage while 4% alcohol arrested the heart, and along with pyruvate was best for preserving functional recovery.

Alterations in the function of cardiac cellular membranes, which control the electrophysiological and mechanical behavior of cardiac muscle, may contribute to the pathogenesis of abnormal cardiac function. Alcohol affects transmembrane ion fluxes of $Na^+$, $K^+$, $Ca^{2+}$, and $Cl^-$ and inhibits the $Na^+/K^+$ and the $Na^+/Ca^{2+}$ exchange, thereby reducing energy dependent processes during the basal state. Alcohol further decreases intracellular $Na^+$ levels, causes dehydration of the myocardial fiber and prevents edema.

As can be seen from the results retention for cardiac function was not related to ATP concentrations, Pi levels, or $[pH]i$. It is possible that the saline solution containing pyruvate and alcohol helped to maintain membrane integrity by influencing ion distribution. Upon reperfusion the hearts reperfused with Roe's cardioplegic solution had a slightly alkaline $[pH]i$. The latter may be due to leaky membranes and inability of the myocardial fibers to maintain the ion gradient. Rapid reversibility of cardiac depression is a desirable feature of a cardioplegic solution. The 4% alcohol caused an immediate arrest and the cardiac depression induced by alcohol was immediately reversible. An immediate arrest may not be crucial for preserving cardiac function since myocardial recovery was nearly as good with the physiological saline having pyruvate as the substrate, as compared to the same solution plus alcohol, and significantly better than a standard cardioplegic solution.

High intracellular calcium $[Ca^{2+}]i$ and low $[pH]i$, which occurs with ischemia, inhibits glycolysis and fatty acid oxidation, resulting in accumulation of intermediates with no provision for synthesis of high energy phosphates. With reperfusion the PCr levels rose in the hearts of the groups which were provided pyruvate. Commensurate with the rise in PCr there was also an increase in oxygen consumption. Inorganic phosphate did not rise excessively high in any of the three groups; the latter is most likely due to the fact that no inorganic phosphate was added to the media.

The results of this study confirm that a saline solution containing 4% ethanol and 10 mM pyruvate preserves cardiac function over a 24 hour period, and that a saline solution containing 10 mM pyruvate partially preserves cardiac function over a 24 hour period.

TABLE II

|  | ATP (mM) | PCr (mM) | Pi (mM) | [pH]i |
|---|---|---|---|---|
| GROUP I [N = 6] | | | | |
| (Solution A) 5% Alcohol and Pyruvate as the substrate | | | | |
| PREISCHEMIA | 9.8 + 1.2 | 11.9 + 1.1 | 3.6 + 0.4 | 7.05 + .02 |
| POSTISCHEMIA | 3.8 + 1.1 | 8.6 + 1.4 | 10.4 + 0.9 | 6.95 + .03 |
| GROUP II [N = 6] | | | | |
| (Solution B) Roe's Cardioplegic Solution | | | | |

TABLE II-continued

|  | ATP (mM) | PCr (mM) | Pi (mM) | [pH]i |
| --- | --- | --- | --- | --- |
| PREISCHEMIA | 10.1 + 0.8 | 12.2 + 2.1 | 3.3 + 1.0 | 7.01 + .02 |
| POSTISCHEMIA | 4.2 + 0.9 | 3.2 + 1.2 | 9.6 + 1.4 | 7.22 + .07 |
| GROUP III [N = 6] | | | | |
| (Solution C) Pyruvate as the substrate and no alcohol | | | | |
| PREISCHEMIA | 9.7 + 1.2 | 11.8 + 2.1 | 3.8 + 0.8 | 7.02 + .03 |
| POSTISCHEMIA | 3.6 + 2.1 | 6.2 + 1.4 | 11.8 + 1.4 | 6.97 + .06 |

EXAMPLE 5

Isolated Pig Heart Preserved for 24 Hours

This example illustrates the utility of the present invention for the preservation of the isolated heart of the higher mammal species.

Pig heart was precannulated as described before and removed from the pig's chest according to procedures described in Example 2. Preischemic measurements were done to determine levels of the same parameters for cardiac function and energy level as in Example 3. Then the heart was perfused for 15 minutes with cardioplegic Solution A and 10 minutes with cardioplegic Solution A. Both perfusions were done at 37° C. The isolated heart was then submerged in a 2 gallon container tightly closed and filled with the Solution 3 for 24 hours at a temperature 4° C. The heart, including cannulae was completely submerged in the solution C which was continuously gently oxygenated with a mixture of 95% of $O_2$ and 5% of $CO_2$. All conditions were kept aseptic and the apparatus was sterilized beforehand. The heart was attached gently to the wall of the container wall so that no mechanical damage occurred during the simulated transportation from the one room to another. After 24 hours, the heart with both cannulae was removed from the container, reattached to the isolated heart apparatus and reperfused with the solution C again. The vital signs were followed.

At that time, more than 90% of the normal cardiac function of the myocardium and more than 70% of the mitochondrial activity was restored, measured by pressure, heart beat, coronary flow and ECG and $^{31}$P-NMR.

What is claimed is:

1. An organ preservation solution suitable for long-term preservation of heart for transplantation, consisting of pyruvate, inorganic salts providing ions to retain the cell action potential across the membrane and a protein selected from the group consisting of albumin and fetal calf serum.

2. The solution of claim 1 wherein the inorganic salts providing the ions are sodium chloride, potassium chloride, calcium chloride, sodium bicarbonate, sodium ethylenediaminetetraacetic acid, and magnesium salt.

3. The solution of claim 2 wherein the protein is synthetic albumin or natural albumin, and magnesium salt is magnesium chloride or magnesium sulfate.

4. The solution of claim 3 comprising 90-120 mM of sodium chloride, 4-4.5 mM of potassium chloride, 0.5-2.5 mM of calcium chloride, 22-28 mM of sodium bicarbonate, 0.0.5 mM of sodium ethylenediaminetetraacetic acid, 0.8-2 mM of magnesium sulfate or magnesium chloride, 6-15 mM of pyruvate and 0.01-1% of fetal calf serum or albumin.

5. The solution of claim 4 comprising 110 mM of sodium chloride, 4.3 mM of potassium chloride, 2 mM calcium chloride, 25 mM sodium bicarbonate, 0.5 mM of sodium ethylenediaminetetraaacetic acid, 1.2 mM of magnesium sulfate, 10 mM of sodium pyruvate and 0.1% of albumin.

6. The solution of claim 5 further containing 5-20% of fluorocarbon.

7. A cardioplegic preservation solution suitable for long-term preservation of heart for transplantation comprising pyruvate, inorganic salts providing ions to retain the heart cell action potential across the membrane, a protein selected from the group consisting of albumin and fetal calf serum or other protein providing viscosity similar to albumin and ethanol.

8. The solution of claim 7 wherein the inorganic salts providing the ions are sodium chloride, potassium chloride, calcium chloride, sodium bicarbonate, sodium ethylenediaminetetraacetic acid, and magnesium salt.

9. The solution of claim 7 wherein the protein is fetal calf serum, synthetic or natural albumin and magnesium salt is magnesium chloride or magnesium sulfate.

10. The solution of claim 7 comprising 110 mM of sodium chloride, 4.3 mM of potassium chloride, 2 mM calcium chloride, 25 mM sodium bicarbonate, 0.5 mM of sodium ethylenediaminetetraacetic acid, 1.2 mM of magnesium sulfate, 10 mM of sodium pyruvate, 4% of ethanol and 0.1% of albumin.

11. The solution of claim 10 further containing 5-20% of fluorocarbon.

12. A method for preservation of the heart for transplantation comprising the perfusion of the heart with a cardioplegic solution consisting of 90-120 mM of sodium chloride, 4-4.5 mM of potassium chloride, 0.5-2.5 mM of calcium chloride, 22-28 mM of sodium bicarbonate, 0.0.5 mM of sodium ethylenediaminetetraacetic acid, 0.8-2 mM of magnesium sulfate or magnesium chloride, 6-15 mM of pyruvate, and 0.01-1% of fetal calf serum or albumin.

13. The method of claim 12 wherein the cardioplegic solution comprises 110 mM of sodium chloride, 4.3 mM of potassium chloride, 2 mM calcium chloride, 25 mM sodium bicarbonate, 0.5 mM of sodium ethylenediaminetetraacetic acid, 1.2 mM of magnesium sulfate, 10 mM of sodium pyruvate, and 0.1% of albumin.

14. The method of claim 13 at least ten minutes of wherein the perfusion is at temperature between 30°-37° C.

15. A method for preservation of the heart for transplantation comprising perfusion of the heart with a cardioplegic solution comprising 90-120 mM of sodium chloride, 4-4.5 mM of potassium chloride, 0.5-2.5 mM of calcium chloride, 22-28 mM of sodium bicarbonate, 0.0.5 mM of sodium ethylenediaminetetraacetic acid, 0.8-2 mM of magnesium sulfate or magnesium chloride, 6-15 mM of pyruvate, 2-8% of ethanol, and 0.01-1% of fetal calf serum or albumin.

16. The method of claim 12 wherein the cardioplegic solution of comprising 100 mM of sodium chloride, 4.3 mM of potassium chloride, 2 mM calcium chloride, 25 mM sodium bicarbonate, 0.5 mM of sodium EDTA, 1.2 mM of magnesium sulfate 10 mM of sodium pyruvate, 4% of ethanol, and 0.1% of albumin.

17. The method of claim 13 wherein the perfusion is at temperature between 4°-37° C.

18. A method for preservation of the heart for transplantation comprising of first perfusion of the heart with cardioplegic solution containing pyruvate at 37° C., followed with a perfusion of the heart with a cardioplegic solution containing pyruvate and ethanol at temperature from 4°-37° C. and storing the heart in a cardioplegic solution containing pyruvate at temperature between 2°-10° C.

19. The method of claim 18 wherein the preservation period is longer than 24 hours.

* * * * *

UNITED STATES PATENT AND TRADEMARK OFFICE
CERTIFICATE OF CORRECTION

PATENT NO. : 5,075,210

DATED : December 24, 1991

INVENTOR(S) : Joan Wikman-Coffelt

It is certified that error appears in the above-identified patent and that said Letters Patent is hereby corrected as shown below:

Column 2, line 29, delete "mEg/l" and insert --mEq/l--.
Column 3, lines 28, 29, 50, 52, and 66, delete "ischaemia" and insert --ischemia--.
Column 4, line 29, delete "ischaemia" and insert --ischemia--.
Column 6, line 43, delete "suggest" and insert --suggests--.
Column 9, line 2, delete "a between" and "temperature".
Col. 9, line 21, change "vasidilation" should read --vasodilation--.
Column 12, line 28, delete "submerging" and insert --submergence--;
line 58, delete "drawings" and insert --drawing--.
Column 13, line 53, delete "continue" and insert --continues--;
line 60, delete "to" and line 65, delete "to the" and insert --to be--.
Column 16, line 39, delete the first "peaks".
Column 17, line 1, delete "disolve" and insert --dissolved--;
line 13, delete first "37";
line 39, delete "u moles" and insert --$\mu$ moles--.
Column 18, line 23, delete "not" and insert --no--;
line 49, delete "no" and insert --not--.
Column 19, line 33, delete "form" and insert --from--;
line 36, delete "wa" and insert --was--.

UNITED STATES PATENT AND TRADEMARK OFFICE
CERTIFICATE OF CORRECTION

PATENT NO. : 5,075,210
DATED : December 24, 1991
INVENTOR(S) : Joan Wikman-Coffelt It is certified that error appears in the above-indentified patent and that said Letters Patent is hereby corrected as shown below:

Claim 4, col. 21, line 6, delete "0.0.5" and insert --0.5--.

Claim 14, col. 22, line 53, after "13" insert --wherein--.

Col. 22, line 54, delete "wherein the".

Signed and Sealed this

Fifth Day of October, 1993

BRUCE LEHMAN

Attesting Officer

Commissioner of Patents and Trademarks